US011717781B2

(12) United States Patent
Jones et al.

(10) Patent No.: US 11,717,781 B2
(45) Date of Patent: Aug. 8, 2023

(54) FILTER CARTRIDGE ASSEMBLY HAVING FLUID MANAGEMENT STRUCTURE

(71) Applicant: Conmed Corporation, Utica, NY (US)

(72) Inventors: Jacob Jones, Lakewood, CO (US); Joseph Allen, Bloomfield, CO (US); Jonathan Teymouri, Aurora, CO (US); Stephanie Retureta, Highlands Ranch, CO (US); Rodney Crain, Denver, CO (US); Mahesh Krishnamoorthy, Parker, CO (US)

(73) Assignee: Conmed Corporation, Largo, FL (US)

(*) Notice: Subject to any disclaimer, the term of this patent is extended or adjusted under 35 U.S.C. 154(b) by 643 days.

(21) Appl. No.: 16/749,371

(22) Filed: Jan. 22, 2020

(65) Prior Publication Data
US 2020/0324238 A1    Oct. 15, 2020

Related U.S. Application Data

(60) Provisional application No. 62/836,116, filed on Apr. 19, 2019, provisional application No. 62/831,933, filed on Apr. 10, 2019.

(51) Int. Cl.
*B01D 46/00*  (2022.01)
*B01D 46/10*  (2006.01)
(Continued)

(52) U.S. Cl.
CPC ....... *B01D 46/0043* (2013.01); *A61M 13/006* (2014.02); *B01D 46/10* (2013.01);
(Continued)

(58) Field of Classification Search
CPC ................ A61M 13/00; A61M 13/006; A61M 2205/3331; A61B 17/34; A61B 17/3421;
(Continued)

(56) References Cited

U.S. PATENT DOCUMENTS 4,735,603 A * 4/1988 Goodson .............. A61B 18/201
606/14
7,182,752 B2 * 2/2007 Stubbs ............... A61B 17/3421
604/164.01
(Continued)

FOREIGN PATENT DOCUMENTS

WO       02-074364 A2    9/2002

OTHER PUBLICATIONS

International Search Report and Written Opinion issued in corresponding PCT Patent Application No. PCT/US2020/023328, dated Jul. 1, 2020.
(Continued)

*Primary Examiner* — Minh Chau T Pham
(74) *Attorney, Agent, or Firm* — Locke Lord LLP; Scott D. Wofsy (57) ABSTRACT

A filter cartridge assembly is disclosed, which includes a housing having a reservoir for collecting fluids entering the housing through a gas return path, a sensor located within the reservoir for detecting a fluid level therein, and a backer plate positioned within the housing adjacent an inlet port to the reservoir and including fluid management structure to shield the sensor from fluid entering the reservoir from the gas return path through the inlet port and causing a false indication of the fluid level in the reservoir.

20 Claims, 7 Drawing Sheets

(51) Int. Cl.
*B01D 46/14* (2006.01)
*A61M 13/00* (2006.01)
*B01D 46/44* (2006.01)

(52) U.S. Cl.
CPC ........ *B01D 46/44* (2013.01); *A61B 2218/008* (2013.01); *A61M 2205/125* (2013.01); *A61M 2205/3306* (2013.01); *A61M 2205/3389* (2013.01); *A61M 2205/7536* (2013.01); *B01D 2279/00* (2013.01)

(58) Field of Classification Search
CPC .......... A61B 17/3474; A61B 2218/008; B01D 46/00; B01D 46/0008
USPC .................. 55/385.1; 604/14, 23, 26, 164.01
See application file for complete search history.

(56) References Cited

U.S. PATENT DOCUMENTS

| | | | | |
|---|---|---|---|---|
| 7,250,035 B1 * | 7/2007 | Ott | ...................... | A61M 13/003 604/26 |
| 7,285,112 B2 * | 10/2007 | Stubbs | ............... | A61B 17/3421 604/23 |
| 7,338,473 B2 * | 3/2008 | Campbell | .......... | A61B 17/3462 604/23 |
| 7,854,724 B2 | 12/2010 | Stearns et al. | | |
| 8,608,816 B2 | 12/2013 | Palmerton et al. | | |
| 9,067,030 B2 | 6/2015 | Stearns et al. | | |
| 9,375,539 B2 | 6/2016 | Stearns et al. | | |
| 9,387,295 B1 | 7/2016 | Mastri et al. | | |
| 9,387,296 B1 * | 7/2016 | Mastri | ................. | A61M 13/006 |
| 9,950,127 B2 * | 4/2018 | Stearns | ............... | A61M 13/003 |
| 2013/0231606 A1 | 9/2013 | Stearns et al. | | |
| 2016/0287817 A1 * | 10/2016 | Mastri | ................. | A61M 13/003 |
| 2017/0000959 A1 | 1/2017 | Mantell et al. | | |
| 2018/0126028 A1 | 5/2018 | Engelhard | | |
| 2019/0001078 A1 | 1/2019 | Kane et al. | | |
| 2019/0388631 A1 * | 12/2019 | Silver | ............... | A61B 17/3421 |
| 2022/0054164 A1 * | 2/2022 | Isshiki | ............... | A61B 17/3421 |

OTHER PUBLICATIONS

Extended European Search Report dated Dec. 5, 2022, issued during the prosecution of European Patent Application No. EP 20786764.9.

* cited by examiner

FILTER CARTRIDGE ASSEMBLY HAVING FLUID MANAGEMENT STRUCTURE

CROSS-REFERENCE TO RELATED APPLICATION

This application claims the benefit of priority to U.S. Provisional Patent Application Ser. No. 62/831,933 filed Apr. 10, 2019 and U.S. Provisional Patent Application Ser. No. 62/836,116 filed Apr. 19, 2019, the disclosure of which are both herein incorporated by reference in their entireties.

BACKGROUND OF THE INVENTION

1. Field of the Invention

The subject invention relates to equipment for use in performing laparoscopic or endoscopic surgery, and more particularly, to a filter cartridge assembly for use with a surgical gas circulation system.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the obturator is removed, and the trocar allows access for instruments to be inserted into the abdominal cavity. Typical trocars provide a pathway to insufflate the abdominal cavity, so that the surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permit ready access to an insufflated surgical cavity without the need for conventional mechanical valve seals, as described, for example, in U.S. Pat. No. 7,854,724, the disclosure of which is herein incorporated by reference in its entirety. These devices are constructed from several nested components including an inner tubular body portion and a coaxial outer tubular body portion. The inner tubular body portion defines a central lumen for introducing conventional laparoscopic surgical instruments to the abdominal cavity of a patient and the outer tubular body portion defines an annular lumen surrounding the inner tubular body portion for delivering insufflation gas to the abdominal cavity of the patient and for facilitating periodic sensing of abdominal pressure.

SurgiQuest, Inc. has also developed a multi-modal gas delivery device for use with its gas sealed surgical access devices that facilitates insufflation, gas recirculation and smoke evacuation, as described in U.S. Pat. No. 9,375,539. The multi-modal gas delivery device communicates pneumatically with the gas sealed access devices and other conventional surgical access devices through a disposable single-use filtered multi-lumen tube set, as described in commonly assigned U.S. Pat. No. 9,067,030.

The filtered multi-lumen tube set includes a filter cartridge having a housing defining an interior reservoir for trapping and collecting fluids drawn into the tube set during smoke evacuation procedures by way of the surgical access device connected thereto. A pair of optical sensor prisms formed integral with the housing are located within the reservoir for sensing liquid levels within the reservoir. These include a first optical prism to detect a first fluid level within the reservoir and a second optical prism for detecting a second fluid level in the reservoir. These optical prisms function as reflective sensors in conjunction with an infrared emitter and photodiode control circuit located within the gas delivery device that produces a visual and/or audible signal indicating that fluid levels within the reservoir have reached certain threshold values.

Figure 2:
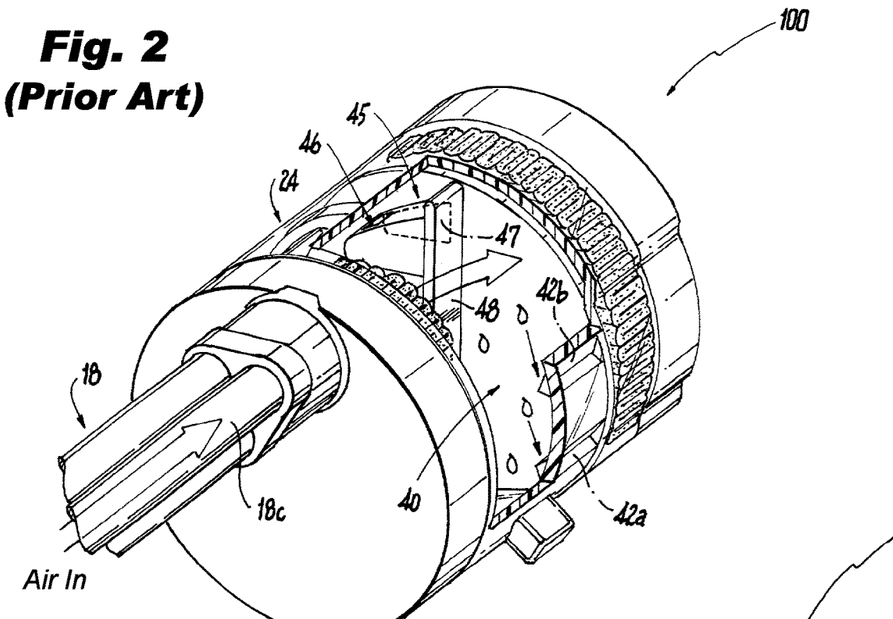
FIG. 2 is a perspective view of a prior art filter cartridge assembly for use with the surgical gas delivery device shown in FIG. 1, with a portion of the outer wall of the cartridge housing cut away to illustrate the problem that arises when fluid entering the reservoir contacts the fluid level sensors located therein causing a false indication of the fluid level in the reservoir.

In both clinical and lab settings, it has been observed that liquid droplets can be formed on the optical prisms due to spraying and splashing of high velocity fluid entering the cartridge housing through the gas return lumen of the tube set, as illustrated in FIG. 2 of the subject application, which depicts a prior art filter cartridge assembly during use. This results in an error message or false indication of the fluid level within the reservoir, when in fact, only a minimal amount of liquid has actually accumulated therein. This false positive error can be a distraction to the surgical staff and can potentially cause an interruption or delay in the surgical procedure.

It has been determined through testing and evaluation that the root cause of these false positive error messages is due the design of the entry pathway into the reservoir of the prior art filter cartridge housing, which does not adequately divert fluid droplets away from the optical prisms located in the reservoir before the fluid has had a chance to accumulate within the bottom of the reservoir.

The subject invention is intended to address this fluid management issue and thereby improve upon the existing filter cartridge design that is currently in use.

SUMMARY OF THE DISCLOSURE

The subject invention is directed to a new and useful filter cartridge assembly for a surgical gas delivery system used during endoscopic and laparoscopic surgical procedures. The cartridge assembly includes a cylindrical housing having an internal reservoir for collecting fluids entering the housing through a gas return path from a patient's body cavity, a sensor located within the reservoir for detecting a fluid level therein, and a circular backer plate positioned within the housing adjacent an inlet port to the reservoir and including fluid management structure to shield the sensor from fluid entering the reservoir from the gas return path through the inlet port and potentially causing a false indication of the fluid level in the reservoir, which would be problematic during a surgical procedure.

The circular backer plate includes an outlet port from the reservoir that is located adjacent an outer periphery of the plate. The backer plate further incudes a radial guard wall that extends from the backer plate into the reservoir for deflecting fluid entering the reservoir away from the outlet port and into the reservoir.

Preferably, the fluid management structure includes a baffle wall that is located adjacent the fluid level sensor to shield the fluid level sensor from fluid entering the reservoir. The baffle wall includes an elongated primary wall section and a secondary wall section that extends angularly away from the primary wall section. The primary and second wall sections of the baffle wall are equally spaced from the sensor.

In an embodiment of the invention, the fluid management structure includes a plurality of spaced apart planar louvers that extend from the guide wall toward the baffle wall to impact the momentum of the fluid laden gas flow in a way that reduces the likelihood that fluids will contact the sensors in the reservoir. In another embodiment of the invention, the fluid management structure includes a plurality of spaced apart posts or bosses that extend outwardly from the backer plate and are arranged between the guard wall and the baffle wall to further impact the momentum of the fluid laden gas entering the reservoir. In yet another embodiment of the invention, the fluid management structure includes a plurality of spaced apart triangular louvers that extend from the guide wall toward the baffle wall.

The subject invention is also directed to a backer plate for use within a filter cartridge assembly, which comprises a circular disc including an outlet port adjacent a radially outer periphery thereof for communicating with a gas return path of the filter cartridge assembly, a guard wall extending radially from the outlet port to deflect fluids away from the outlet port and into a reservoir defined with the filter cartridge assembly and a baffle wall spaced apart from the guard wall to shield a fluid level sensor located within the reservoir from fluids entering the reservoir through an inlet port to the reservoir.

These and other features of the filter cartridge assembly of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the filter cartridge assembly of the subject invention without undue experimentation, preferred embodiments thereof will be described in detail herein below with reference to the figures wherein.

DETAILED DESCRIPTION OF THE PREFERRED EMBODIMENTS

Figure 1:
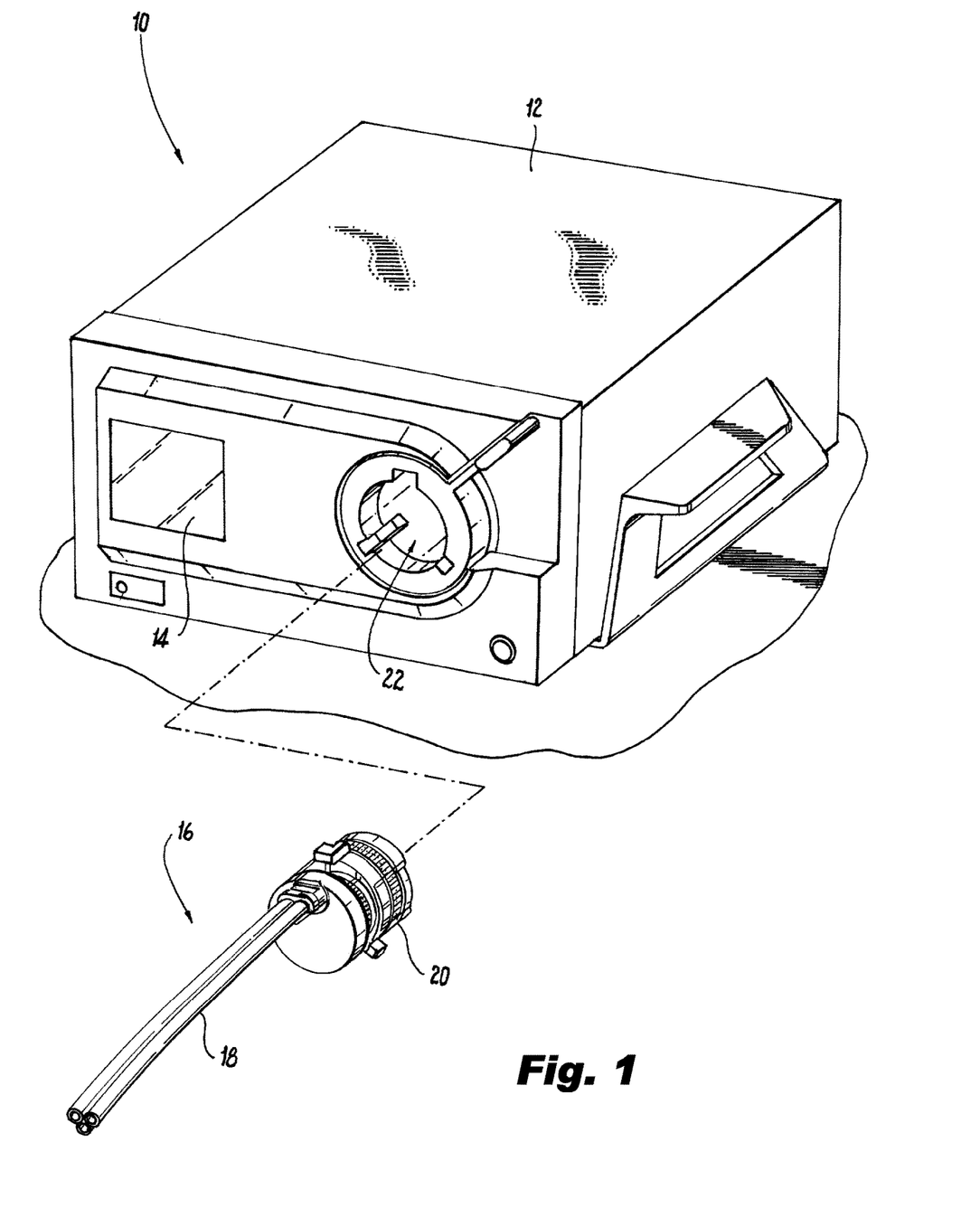
FIG. 1 is a perspective view of a gas circulation system that includes a multi-modal surgical gas delivery device and a tri-lumen filtered tube set constructed in accordance with a preferred embodiment of the subject invention.

Referring now to the drawings wherein like reference numerals identify similar structural elements and features of the subject invention, there is illustrated in FIG. 1 a gas circulation system 10 for performing an endoscopic surgical procedure in a surgical cavity of a patient, and more particularly, for performing a laparoscopic surgical procedure in the abdominal cavity of a patient.

The gas circulation system 10 includes a programmable multi-modal gas delivery device 12. The gas delivery device 12 is of the type described in commonly assigned U.S. Pat. No. 9,375,539, the disclosure of which is herein incorporated by reference in its entirety. The gas delivery device 12 includes a graphical user interface 14 for setting operating parameters to facilitate the introduction of insufflation gas to the surgical cavity of a patient and the recirculation of pressurized gas relative to the surgical cavity of the patient by way of a filtered tube set 16. The device is also designed to facilitate smoke evacuation from the body cavity of a patient during a surgical procedure.

The filtered tube set 16 includes a tri-lumen portion 18 and a filter cartridge assembly 20 of the type disclosed for example in commonly assigned U.S. Pat. No. 9,067,030, the disclosure of which is herein incorporated by reference in its entirety. The tri-lumen portion 18 of the filter cartridge assembly 20 includes an insufflation/sensing lumen 18a, a gas delivery lumen 18b and a gas return lumen 18c. The filter cartridge assembly 20 of the filtered tube set 16 is adapted and configured to interface with a reception port 22 in the front face of the gas delivery device 12.

Figure 3:
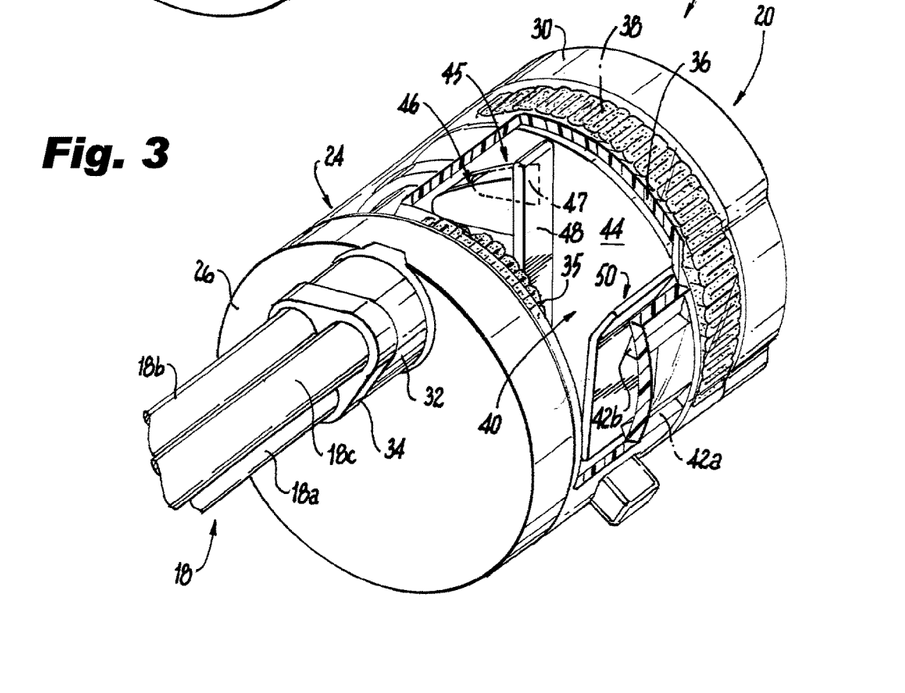
FIG. 3 is a perspective view of the filter cartridge assembly of the subject invention, with a portion of the outer wall of the cartridge housing wall cut away to illustrate the fluid management structure on the backer plate that shield the fluid level sensors located within the reservoir of the cartridge housing.
Figures 4, 5:
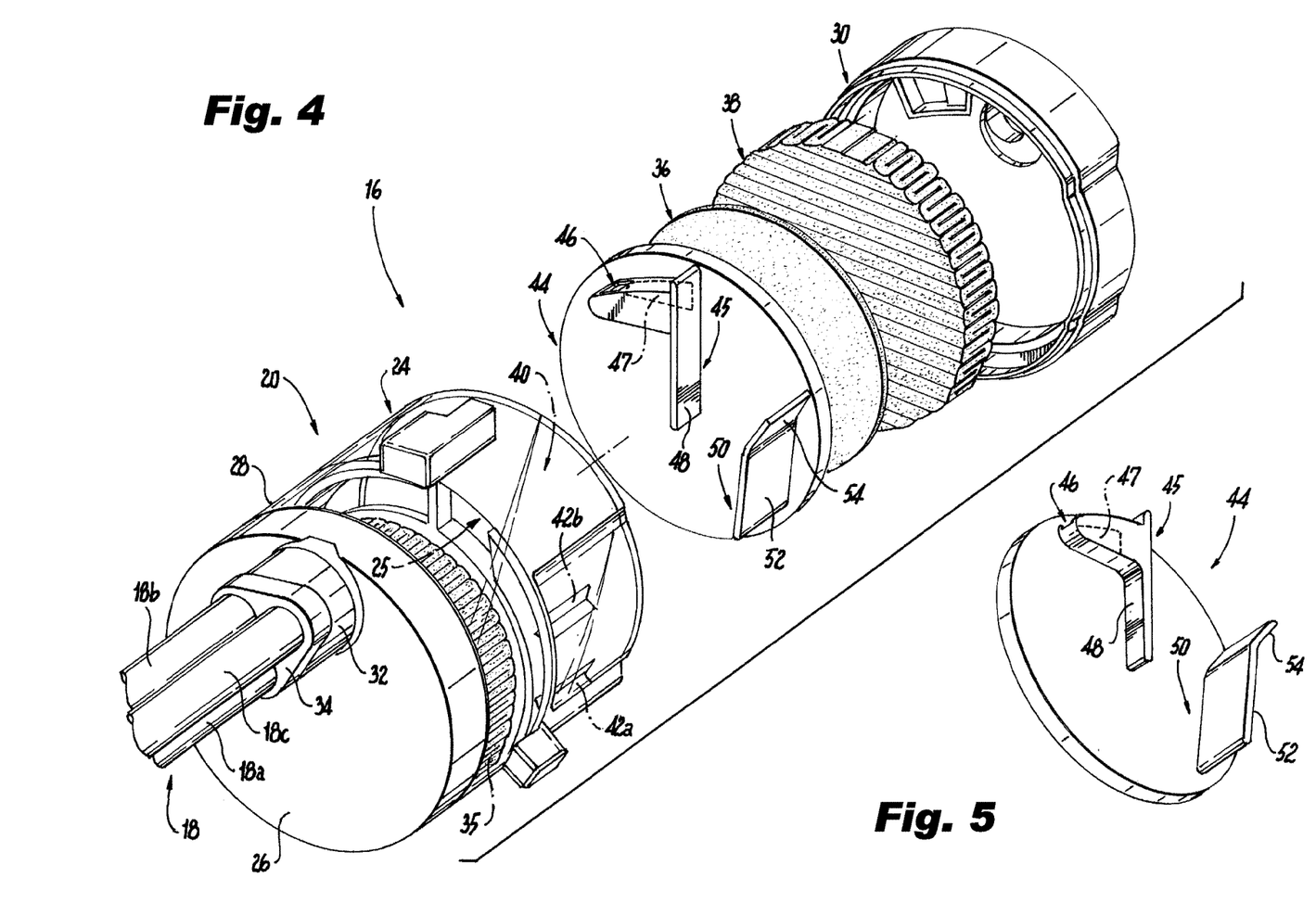
FIG. 4 is an exploded perspective view of the filter cartridge assembly shown in FIG. 3, with parts separated for ease of illustration, wherein the backer plate is shown with the fluid management baffle.
FIG. 5 is a perspective view of the backer plate shown in FIG. 4.

Referring to FIGS. 3 and 4, the filter cartridge assembly 20 of the filtered tube set 16 has a generally cylindrical filter housing 24 that includes a front end cap 26, a central body portion 28 and a rear end cap 30. The central body portion 28 of housing 24 can be made from a transparent material to enable visual inspection of the interior of the cartridge if necessary. The front end cap 26 of housing 24 has a manifold connection 32 for receiving a fitting 34 associated with the tri-lumen tube set 18. While not shown in the drawings, the rear end cap 30 of housing 24 has a plurality of ports formed therein to accommodate gas flowing into and out of the cartridge assembly 20.

The central body portion 28 of housing 24 houses a front pleated filter element 35 adjacent the front end cap 26, an optional central carbon filter element 36 and a rear pleated filter element 38 adjacent the rear end cap 30. Additional filter elements may also be provided within the housing 24 of filter cartridge assembly 20.

The central body portion 28 of filter housing 24 also defines an interior fluid trap or reservoir 40. The reservoir 40 has an upstream inlet port 25 that communicates with the gas return lumen 18c of the tri-lumen portion 18 by way of a gas return path extending through the cartridge housing 24. The reservoir 40 is designed to collect bodily fluids that have been drawn into the housing 24 as fluid laden or humidified gas. This can occur when the gas delivery device 12 is operating in a gas recirculation mode or a smoke evacuation mode.

A circular backer plate 44 is positioned within the central body portion 28 of housing 24 adjacent the upstream inlet port 25 to the reservoir 40. A downstream outlet port 47 of the reservoir 40 is formed in the backer plate 44 adjacent a radial outer periphery thereof. The outlet port 47 communicates with an exit passage 46 of the backer plate 44 and directs gas from the reservoir back into the gas return path that extends through the cartridge housing 24.

The backer plate 44 further includes a fluid management feature 45 in the form of a radially extending guard wall 48 that extends from the exit passage 46 of backer plate 44 and down into the reservoir 40. The guard wall 48 is positioned to deflect fluids entering the reservoir 40 away from the exit passage 46 and outlet port 47 and down into the bottom of the reservoir 40. This will prohibit fluids from traversing through the reservoir 40 and traveling back into the gas return path to head downstream toward the rear pleated filter element 35.

A pair of triangular optical prisms 42a, 42b extending radially inwardly from an interior wall of the filter housing 24 and are located within the reservoir 40 for sensing a level of liquid within the reservoir 40. Preferably, the first or lower prism 42a defines a first set point level for a sensing system and the second or upper prism 42b defines a second set point level for a sensing system. More particularly, as disclosed in U.S. Pat. No. 9,067,030, the first prism 42a is positioned to detect a first liquid level within the reservoir 40 and the second prism 42b is positioned to detect a second liquid level the within reservoir 40.

In operation, an infrared signal is directed into an optical prism 42a, 42b. If, the prism is not covered by liquid in reservoir 40, it will return 100% of the infrared signal, and the system will continue to operate without an alarm. If however, a prism is covered by liquid in reservoir 40, a portion of the infrared light will be scattered into the fluid, and the prism will return less than 100% of the infrared signal. In this case, a visual and/or audible warning will be provided to the surgical staff indicating that the liquid level within the reservoir 40 has reached a threshold level.

In both clinical and lab settings, it had been observed in prior art filter cartridges such as the filter cartridge assembly 100 which is illustrated in FIG. 2, that liquid droplets can form on the optical prisms 42a, 42b due to spraying and splashing of high velocity fluid laden gas entering the cartridge housing 24 through the gas return lumen 18c by way of inlet port 25. This results in an error message or false indication of the fluid level within the reservoir 40, when in fact, only a minimal amount of liquid has actually accumulated therein. This false positive error can be a distraction to the surgical staff and can potentially cause an interruption or delay in the surgical procedure.

It has been determined through testing and evaluation that the root cause of these false positive error messages is due the design of the entry path into the reservoir 40 of the prior art filter cartridge assembly 100, which does not adequately divert or deflect fluid droplets and spray away from the optical prisms 42a, 42b located in the reservoir 40 before the fluid has had a chance to accumulate within the bottom of the reservoir 40, as illustrated in FIG. 2

Figure 6:
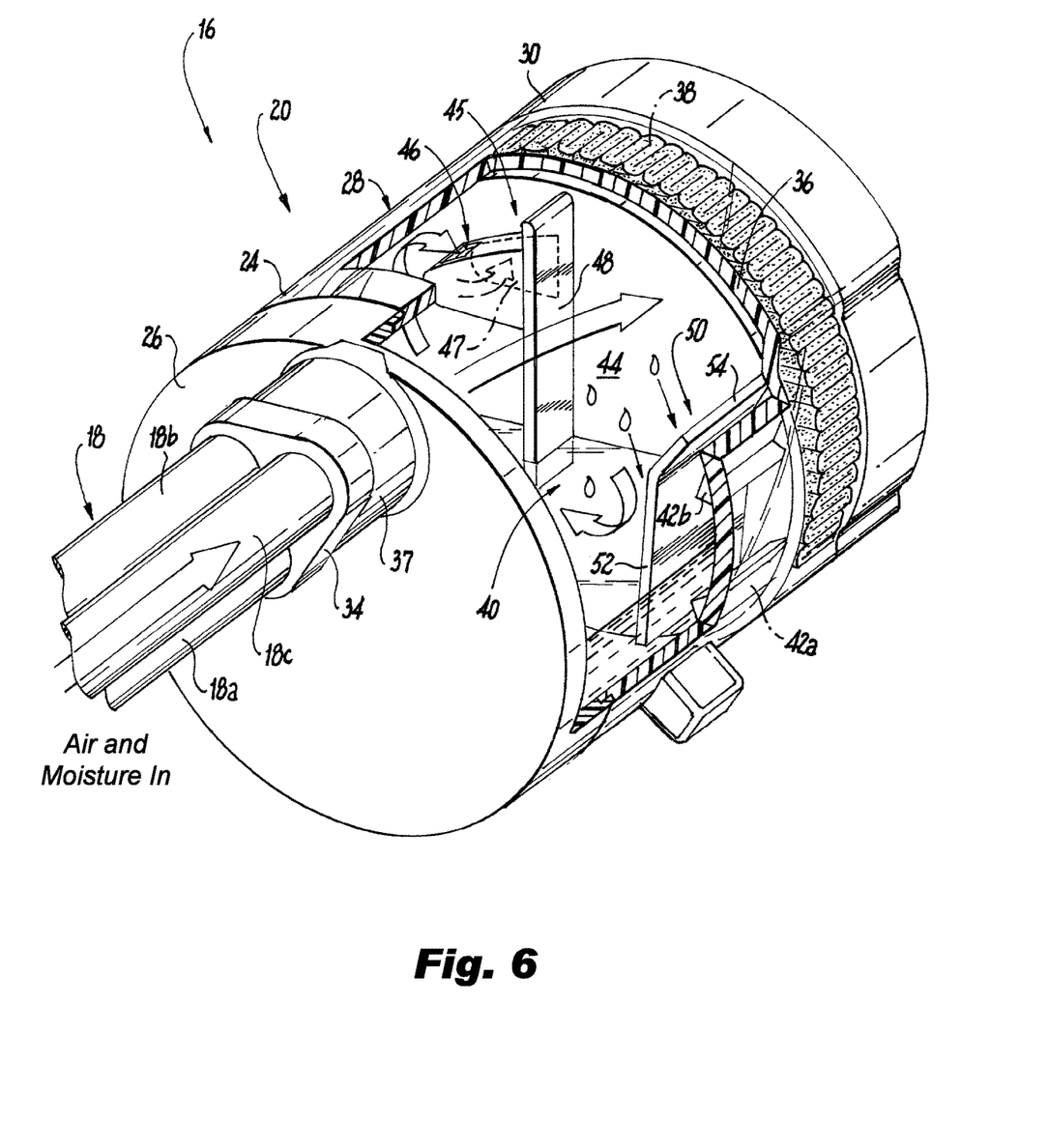
FIG. 6 is a perspective view of the filter cartridge assembly of the subject invention with a portion of the outer wall of the cartridge housing cut away to illustrate how the fluid management baffle on the backer plate shields the fluid level sensors from fluid entering the reservoir.

To address this issue, in the filter cartridge assembly 20 of the subject invention, which is shown in FIGS. 3 through 6, the circular backer plate 44 is provided with fluid management structure to shield the optical prisms 42a, 42b from fluid entering the reservoir 40 through the upstream inlet port 25 and potentially causing a false indication of the fluid level in the reservoir 40. More particularly, the backer plate 44 includes a baffle wall 50 that is located adjacent the optical prisms 42a, 42b to shield them from fluids entering the reservoir 40 through the inlet port 25, as best seen in FIG. 6. In essence, the baffle wall 50 creates a separate chamber within the reservoir 40 in which the optical sensors 42a, 42 by are located and protected from incoming fluid spray that may be deflected off the interior surface of the backer plate 44 or the guard wall 48.

The baffle wall 50 includes an elongated primary wall section 52 and a secondary wall section 54 that extends angularly away from the primary wall section 52. The primary and second wall sections 52, 54 of the baffle wall 50 are preferably equally spaced from the optical prisms 42a, 42b. However, this spacing and the axial height and radial length of the baffle wall sections can vary by design optimization.

Figure 7:
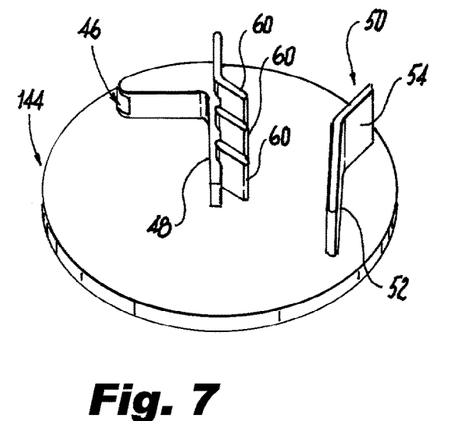
FIG. 7 is a perspective view of the filter cartridge of the subject invention, with a portion of the outer wall of the cartridge housing cut away to illustrate another embodiment of the fluid management structures of the backer plate.
Figure 8:
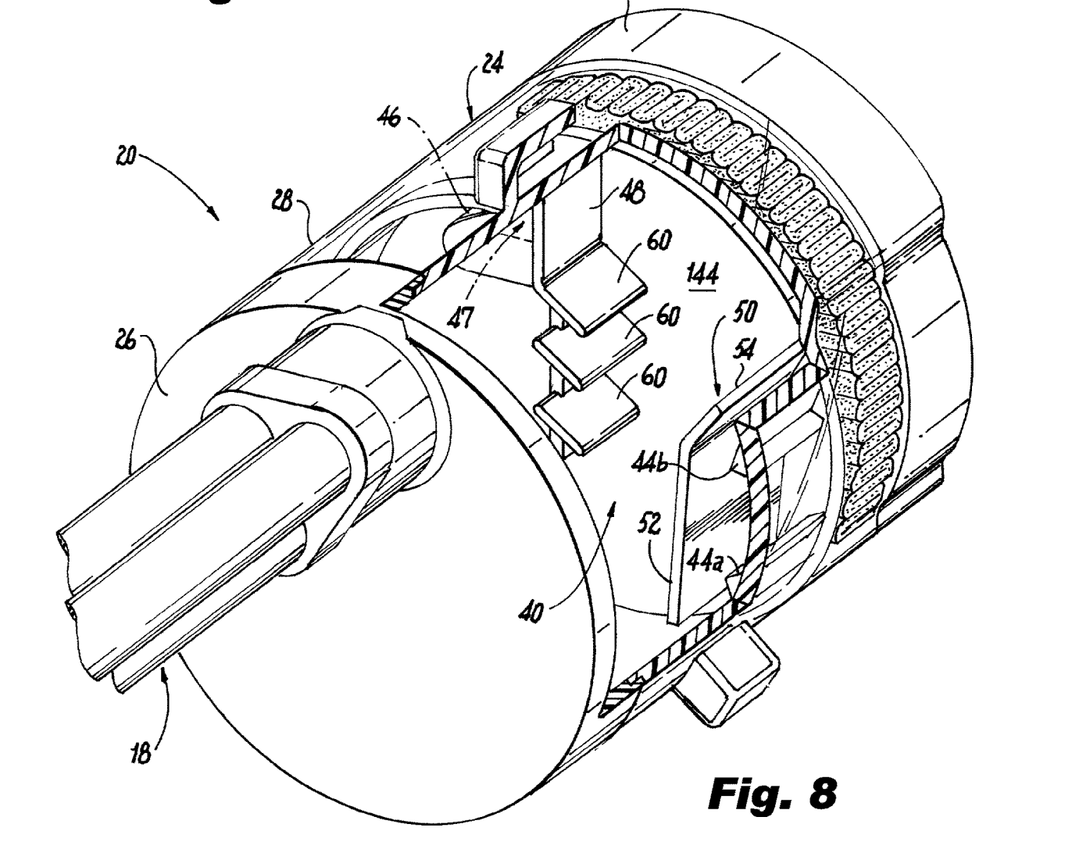
FIG. 8 is a perspective view of the backer plate shown in FIG. 7, illustrating the fluid management structures that include a baffle wall and planar louvers associated with the guard wall.

In another embodiment of the invention shown in FIGS. 7 and 8, the fluid management structure of a baffle plate designated as reference numeral 144 includes a plurality of spaced apart planar louvers 60 that extend angularly way from the guard wall 48 and towards the baffle wall 50. The louvers 60 are designed to divert or otherwise redirect fluid entering the reservoir from the inlet port 25 away from the baffle wall 50 and down into the bottom of the reservoir 40.

Figure 9:
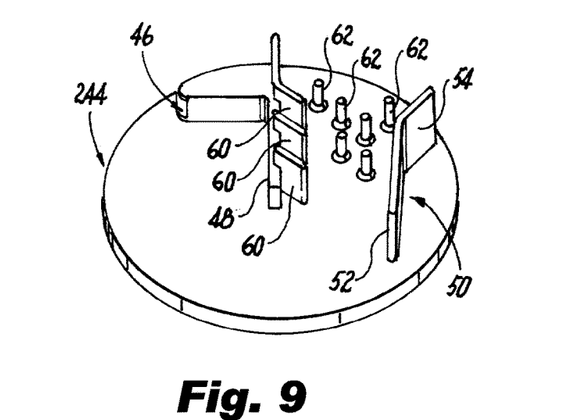
FIG. 9 is a perspective view of the filter cartridge of the subject invention, with a portion of the outer wall of the cartridge housing cut away to illustrate still another embodiment of the fluid management structures of the backer plate.
Figure 10:
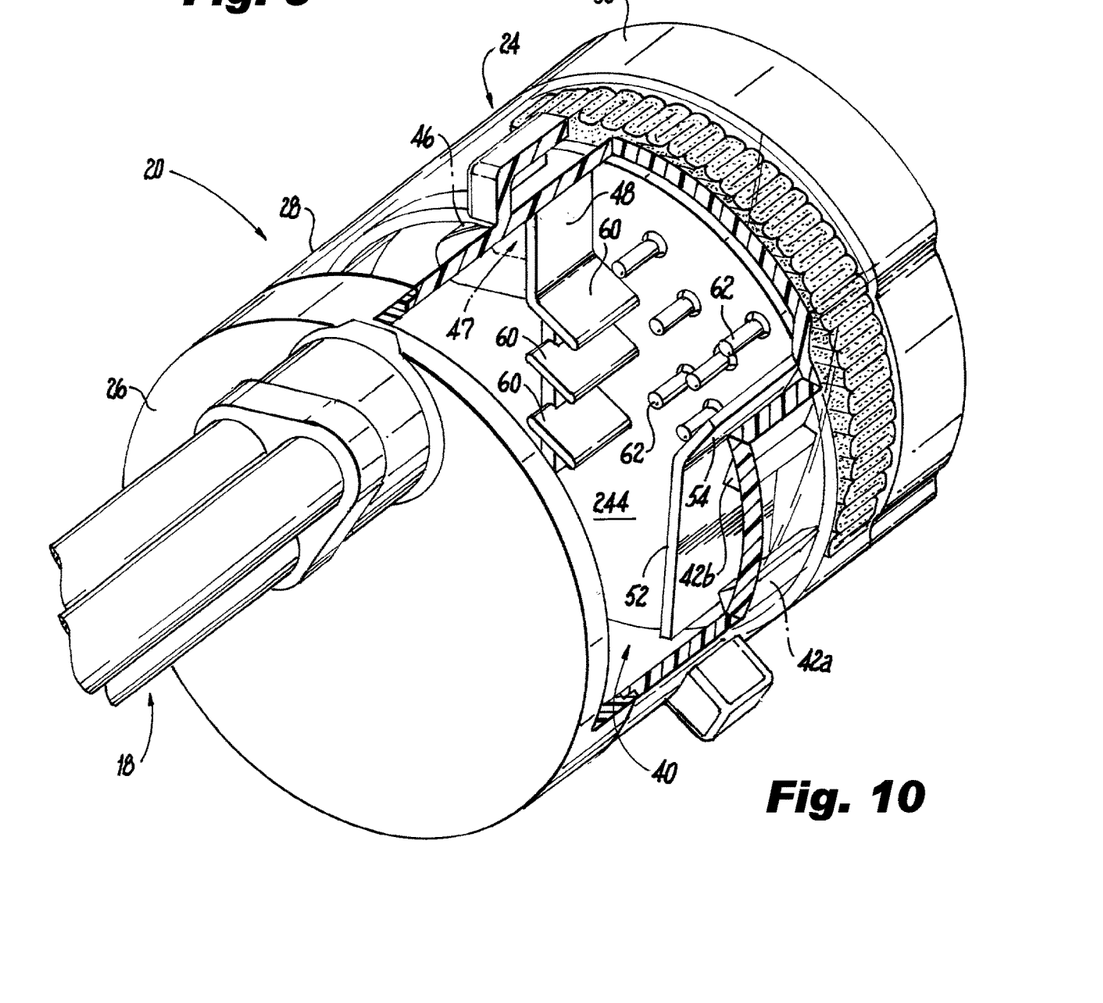
FIG. 10 is a perspective view of the backer plate shown in FIG. 9, illustrating the fluid management structures that include a baffle wall, planar louvers associated with the guard wall and a plurality of spaced apart posts arranged between the baffle wall and the planar louvers.

In still another embodiment of the invention shown in FIGS. 9 and 10, the fluid management structure of a baffle plate designated as reference numeral 244 includes a plurality of spaced apart posts or bosses 62 that are arranged between the louvers 60 and the baffle wall 50. The posts 62 are designed to create turbulence in the fluid laden gas flow entering the reservoir through the inlet port 25 in a way that advantageously reduces the momentum of the flow and enhances the probability that fluids will collect at the bottom of the reservoir 40, without spraying onto optical prisms 42*a*, 42*b*.

Figure 11:
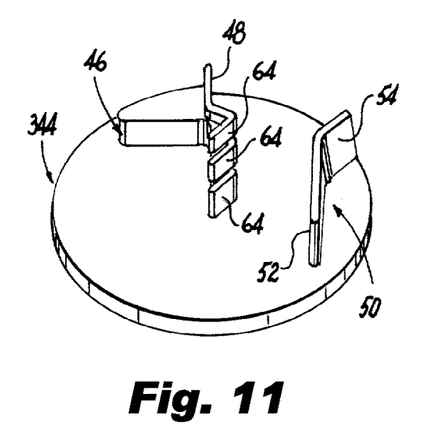
FIG. 11 is a perspective view of the filter cartridge of the subject invention, with a portion of the outer wall of the cartridge housing cut away to illustrate yet another embodiment of the fluid management structures of the backer plate.
Figure 12:
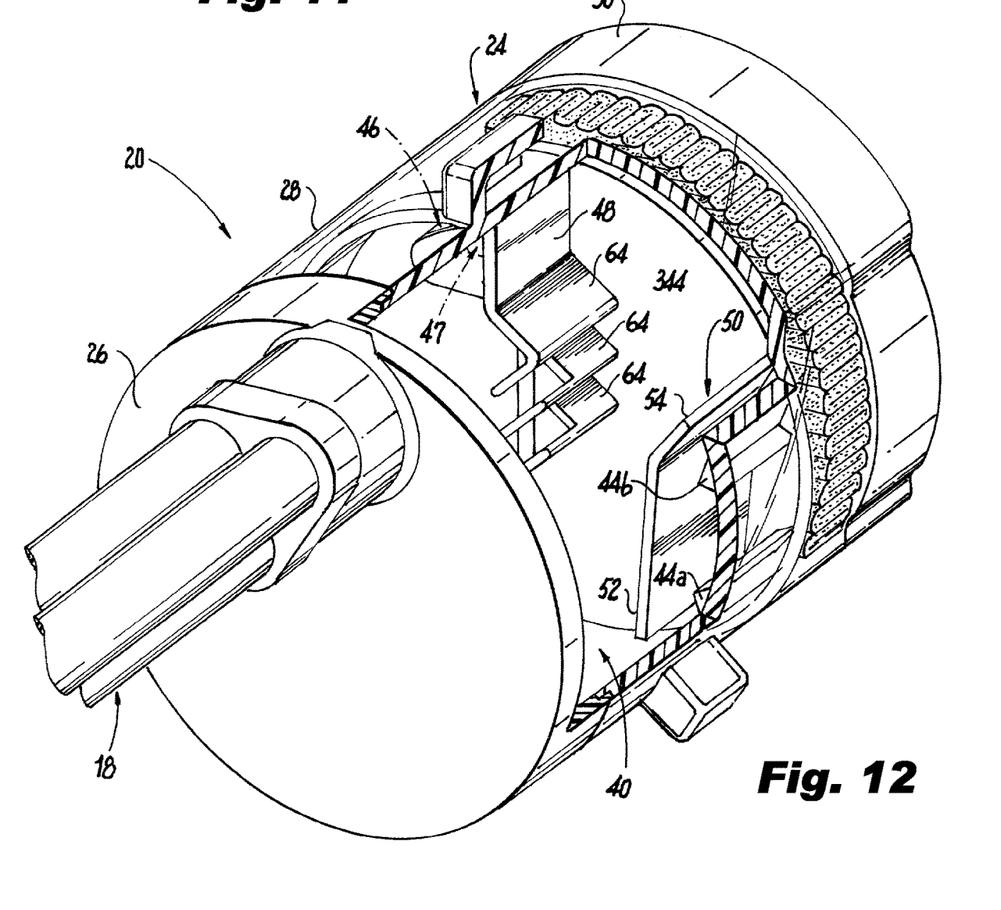
FIG. 12 is a perspective view of the backer plate shown in FIG. 11, illustrating the fluid management structures that include a baffle wall and triangular louvers associated with the guard wall.

In yet another embodiment of the invention shown in FIGS. 11 and 12, the fluid management structure of a baffle plate designated as reference numeral 344 includes a plurality of spaced apart triangular louvers 64 that extend angularly away from the guard wall 48 towards the baffle wall 50. These triangular louvers 64 are designed to more effectively deflect or otherwise redirect fluid entering the reservoir from the inlet port 25 away from the baffle wall 50 and down into the bottom of the reservoir 40, without spraying onto optical prisms 42*a*, 42*b* to cause a false positive error message.

While the subject disclosure has been shown and described with reference to preferred embodiments, those skilled in the art will readily appreciate that changes and/or modifications may be made thereto without departing from the scope of the subject disclosure.

What is claimed is:

1. A filter cartridge assembly, comprising:
   a) a housing including a reservoir for collecting fluids entering the housing through a gas return path;
   b) a sensor located within the reservoir for detecting a fluid level therein; and
   c) a backer plate positioned within the housing adjacent an inlet port to the reservoir and including fluid management structure to shield the sensor from fluid entering the reservoir from the gas return path through the inlet port and causing a false indication of the fluid level in the reservoir, wherein the backer plate includes an outlet port from the reservoir and a radial guard wall that extends from a front surface of the backer plate into the reservoir for deflecting fluids entering the reservoir away from the outlet port and into the reservoir, and wherein the fluid management structure includes a baffle wall that extends from the front surface of the backer plate adjacent the fluid level sensor to shield the fluid level sensor from fluid entering the reservoir.

2. A filter cartridge assembly as recited in claim 1, wherein the baffle wall includes an elongated primary wall section and a secondary wall section that extends angularly away from the primary wall section.

3. A filter cartridge assembly as recited in claim 2, wherein the primary and second wall sections of the baffle wall are equally spaced from the sensor.

4. A filter cartridge assembly as recited in claim 1, wherein the fluid management structure further includes a plurality of spaced apart planar louvers extending from the guard wall toward the baffle wall.

5. A filter cartridge assembly as recited in claim 1, wherein the fluid management structure further includes a plurality of spaced apart posts extending outwardly from the backer plate and arranged between the guard wall and the baffle wall.

6. A filter cartridge assembly as recited in claim 3, wherein the fluid management structure further include a plurality of spaced apart triangular louvers extending from the guard wall toward the baffle wall.

7. A filter cartridge assembly as recited in claim 1, wherein the sensor includes primary and secondary optical prisms extending radially inwardly from an interior wall of the housing into the reservoir.

8. A filter cartridge assembly as recited in claim 1, wherein at least one filter element is located within the housing downstream from the outlet port from the reservoir.

9. A filter cartridge assembly for a surgical gas delivery system, comprising:
   a) a housing including a reservoir for collecting fluids entering the housing through a gas return path from a patient's body;
   b) a pair of sensors located within the reservoir for detecting fluid levels within the reservoir; and
   c) a backer plate positioned within the housing adjacent an inlet port to the reservoir and including an outlet port from the reservoir, the backer plate having a radial guard wall that extends from a front surface of the backer plate into the reservoir for deflecting fluids entering the reservoir from the gas return path through the inlet port away from the outlet port and having a baffle wall that extends from the front surface of the backer plate and is spaced apart from the guard wall to shield the sensors from fluids entering the reservoir from the gas return path through the inlet port and causing a false indication of the fluid level in the reservoir.

10. A filter cartridge assembly as recited in claim 9, wherein the baffle wall includes an elongated primary wall section and a secondary wall section that extends angularly away from the primary wall section.

11. A filter cartridge assembly as recited in claim 10, wherein the primary and secondary wall sections of the baffle wall are equally spaced from the sensors.

12. A filter cartridge assembly as recited in claim 9, wherein a plurality of spaced apart planar louvers extend from the guard wall toward the baffle wall.

13. A filter cartridge assembly as recited in claim 9, wherein a plurality of spaced apart posts extending outwardly from the backer plate are arranged between the guard wall and the baffle wall.

14. A filter cartridge assembly as recited in claim 9, wherein a plurality of spaced apart triangular louvers extend from the guard wall toward the baffle wall.

15. A filter cartridge assembly as recited in claim 9, wherein the sensors include primary and secondary optical prisms extending radially inwardly from an interior wall of the housing into the reservoir.

16. A filter cartridge assembly as recited in claim 9, wherein at least one filter element is located within the housing downstream from the outlet port of the reservoir.

17. A backer plate for a filter cartridge assembly, comprising:
   a circular disc including an outlet port adjacent a radially outer periphery thereof for communicating with a gas return path of the filter cartridge assembly, a guard wall extending outwardly from a front surface of the disc and radially from the outlet port to deflect fluids away from the outlet port and into a reservoir defined with the filter cartridge assembly and a baffle wall extending outwardly from the front surface of the disc and spaced apart from the guard wall to shield a fluid level sensor located within the reservoir from fluids entering the reservoir through an inlet port to the reservoir.

18. A backer plate for a filter cartridge assembly as recited in claim 17, wherein the baffle wall includes an elongated primary wall section and a secondary wall section that extends angularly away from the primary wall section.

19. A filter cartridge assembly, comprising:
a) a housing including a reservoir for collecting fluids entering the housing through a gas return path;
b) a sensor located within the reservoir for detecting a fluid level therein; and
c) a backer plate positioned within the housing adjacent an inlet port to the reservoir and including fluid management structure to shield the sensor from fluid entering the reservoir from the gas return path through the inlet port and causing a false indication of the fluid level in the reservoir, wherein the backer plate includes an outlet port from the reservoir and a radial guard wall extends from the backer plate into the reservoir for deflecting fluids entering the reservoir away from the outlet port and into the reservoir, wherein the fluid management structure includes a baffle wall adjacent the fluid level sensor to shield the fluid level sensor from fluid entering the reservoir, and a plurality of spaced apart planar louvers that extend from the guard wall toward the baffle wall.

20. A filter cartridge assembly, comprising:
a) a housing including a reservoir for collecting fluids entering the housing through a gas return path;
b) a sensor located within the reservoir for detecting a fluid level therein; and
c) a backer plate positioned within the housing adjacent an inlet port to the reservoir and including fluid management structure to shield the sensor from fluid entering the reservoir from the gas return path through the inlet port and causing a false indication of the fluid level in the reservoir, wherein the backer plate includes an outlet port from the reservoir and a radial guard wall extends from the backer plate into the reservoir for deflecting fluids entering the reservoir away from the outlet port and into the reservoir, wherein the fluid management structure includes a baffle wall adjacent the fluid level sensor to shield the fluid level sensor from fluid entering the reservoir, and a plurality of spaced apart posts that extend outwardly from the backer plate and are arranged between the guard wall and the baffle wall.

* * * * *